US000001510H

United States Statutory Invention Registration [19]

[11] Reg. Number: H1510

Collignon et al.

[45] Published: Dec. 5, 1995

[54] CONTINUOUS PROCESS FOR CRYSTALLIZING NITROGUANIDINE

[75] Inventors: Steven L. Collignon; Kerry L. Wagaman, both of Waldorf, Md.

[73] Assignee: The United States of America as represented by the Secretary of the Navy, Washington, D.C.

[21] Appl. No.: 210,881

[22] Filed: Jun. 23, 1988

[51] Int. Cl.[6] ..... C07C 277/08

[52] U.S. Cl. ..... 564/242

*Primary Examiner*—Robert L. Stoll
*Assistant Examiner*—John M. Covert
*Attorney, Agent, or Firm*—Kenneth E. Walden

[57] ABSTRACT

A continuous process for forming spheroidal high bulk density nitroguanidine crystals from an aqueous solution of nitroguanidine which contains methylcellulose and partially hydrolyzed poly(vinyl alcohol) as crystal habit modifiers. A saturated aqueous solution of nitroguanidine is formed at a temperature $T_1$ where 70° C.$\leqq T_1 \leqq$100° C. and crystallization occurs at a lower temperature $T_2$ where 20° C.$\leqq T_1 - T_2 \leqq$50° C.

8 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

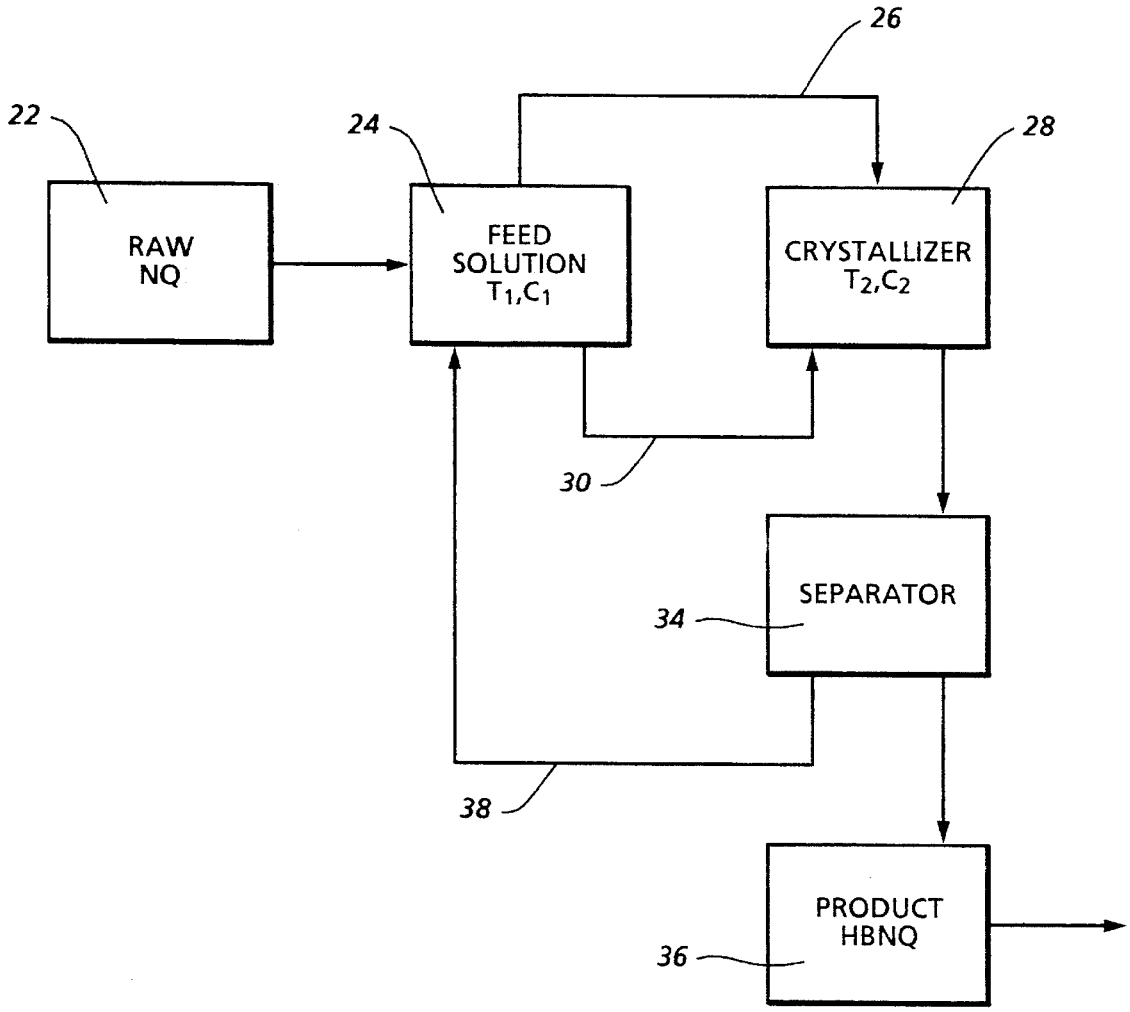
26
22
24
28
RAW
NQ
FEED
SOLUTION
$T_1,C_1$
CRYSTALLIZER
$T_2,C_2$
30
SEPARATOR
34
38
PRODUCT
HBNQ
36

CONTINUOUS PROCESS FOR CRYSTALLIZING NITROGUANIDINE

BACKGROUND OF THE INVENTION

This invention relates to guanidines and more particularly to nitroguandine.

Nitroguanidine is a mass detonating explosive. It is a white crystalline powder with a specific gravity of 1.77. Tests conducted at the Naval Ordnance Laboratory in White Oak, Maryland, (Feb. 1968) showed that in its range of detonability, nitroguanidine behaves as a group I Explosive Class 1, Division 1 (Old Class 7), DOT Class A. This means that it is a mass detonating hazard. The entire quantity will explode virtually instantaneously when a small portion is subjected to the impulse of an initiating agent, or to the effect of a considerable discharge of energy from without, or from sympathetic detonation or propagation. Such an explosion normally will cause severe structural damage to adjacent objects and the simultaneous explosion of other separated explosives and ammunition placed sufficiently close to the initially exploding mass. Casting powder, bulk explosives such as TNT, HMX, RDX, and most warheads and bombs are in this class.

Nitroguanidine is a powerful high explosive which when incorporated in a propellant in appreciable quantities, results in a propellant that burns in a gun with a temperature so cool that a little muzzle flash is produced. Nitroguanidine was first prepared by Jousselin in 1877, and found its original application in cool, burning triple-base, Naval gun propellants in trench mortar shells. Its principal use, however, is in smokeless propellant, due to its property of eliminating flash. In later years nitroguanidine has been developed as an ingredient in propellants for rockets and missiles. High bulk density nitroguanidine (HBNQ) is prepared for these later applications.

Nitroguanidine exists in at least 2 crystal forms: an alpha and a beta. The alpha form crystallizes from hot water as long, thin, flexible, lustrous needles which are tough and pulverize with difficulty. It is the form most commonly used in the explosive industry. The beta form crystallizes from hot water in fern-like clusters of small, thin, elongated plates. The beta form may, be converted into the alpha by dissolution in concentrated sulfuric acid and drowning in water.

A communitor with a hammer speed of 7500 RPM is used to reduce the HBNQ particles to desired size. There are two variables to control the particle size: screen size and feed rate. By keeping the screen and hammer speed constant, but changing to a heavier gauge screen, a smaller particle size is achieved. Therefore, when going to heavier gauge screens for greater strength, it is necessary to increase the size of the opening if the same product size is needed. A uniform feed rate is essential for uniform end product. A built-in feeder permits continuous operation and maximum performance. Once the communitor is set to deliver a certain product it will continue to produce exactly the same results. This last step is very labor-consuming and has a high potential for exploding during the crushing and also the drying operations. Also, the convection oven drying of the nitroguanidine releases undesirable organic chemicals into the environment.

Moreover, the HBNQ which is produced by these prior art methods is rodshaped or needleshaped and therefore difficult to use in explosive manufacturing processes such as extrusion and melt casting.

It would be desirable to provide a continuous process for producing round ovate or spheroidal high bulk density nitroguandine crystals.

SUMMARY OF THE INVENTION

Accordingly, an object of this invention is to provide high bulk density nitroguanidine.

Another object of this invention is to provide a safer method of producing high bulk density nitroguanidine.

A further object of this invention is to eliminate the need for reducing nitroguanidine particle size by hammering.

Yet another object of this invention is to provide a method which will produce spheroidal rather than rodshaped or needleshaped nitroguanidine crystals.

A still further object of this invention is to provide a continuous process for producing spheroidal high bulk density nitroguanidine.

These and other objects of this invention are accomplished by providing:

A continuous process for recrystallizing nitroguandine comprising the following steps in order:

(1) forming a saturated aqueous nitroguanidine solution at a constant temperature $T_1$ which is in the range of from about 70° C. to about 100° C. wherein the solution also contains from 0.5 to 2.0 weight percent of methylcellulose and from 0.5 to 2.0 weight percent of a partially hydrolyzed poly(vinyl alcohol);

(2) feeding the solution formed in step (1) into a crystallizer containing a saturated aqueous solution of nitroguanidine which is maintained at a constant temperature of $T_2$ wherein $20° C. \leqq T_1 - T_2 \leqq 50° C.$ and wherein the methylcellulose and partially hydrolyzed poly(vinyl alcohol) concentrations are the same as in the feed solution;

(3) separating the product spheroidal or ovate nitroguanidine crystals from the supernatant aqueous nitroguanidine solution; and (4) recycling the separated supernatant aqueous nitroguanidine solution to be used again in step (1).

BRIEF DESCRIPTION OF THE DRAWING

Other objects and many of the attendant advantages of the present invention will be readily appreciated as the same becomes better understood by reference to the following detailed description when considered in connection with the accompanying drawing wherein:

The FIGURE is a block diagram of the equipment used in the general continuous process.

DETAILED DESCRIPTION OF THE PREFERRED EMBODIMENT

The present process is used to convert needleshaped, rodshaped, or jagged granular nitroguanidine (NQ) crystals into spheroidal or ovate (egg-shaped) high bulk density nitroguanidine (HBNQ). In addition to higher bulk densities, the round HBNQ spheroidal or ovate crystals produce explosive compositions which are easier to process (mix, extrude, etc.) than do the sharp, jagged NQ crystals.

The present process uses an aqueous solution of nitroguanidine with methylcellulose and partially hydrolyzed poly(vinyl alcohol) as crystal habit modifiers. Referring to the FIGURE, a saturated aqueous solution of nitroguanidine at a temperature of $T_1$ and corresponding saturation concentration of $C_1$ is fed from a feed solution reservoir 24 through feed stream line 26 to a crystallizer 28. The aqueous nitroguanidine solution in the crystallizer 28 is maintained at a constant temperature $T_2$ with corresponding saturation concentration $C_2$ where $T_1>T_2$ and $C_1>C_2$. The solution in the crystallizer 28 is well agitated by suitable means such as a high speed stirrer. In maintaining the constant temperature $T_2$ in the crystallizer 28, the following factors come into play: (1) the size of the crystallizer 28, (2) the rate of feed of solution from line 26, and (3) the use of cooling means.

Supernatant liquid is removed from the crystallizer 28 and returned through line 30 to the feed solution resevoir 24. A slurry of HBNQ crystals and aqueous nitroguanidine solution is transferred from the crystallizer 28 through product stream line 32 to a separator 34 where the HBNQ crystals are removed and placed into storage 36. The remaining supernatant liquid is transferred from the separator 34 through line 38 to the feed solution reservoir 24.

In the feed solution reservoir 24, the temperature and nitroguanidine concentration of the solutions from lines 30 and 38 are raised again to $T_1$ and $C_1$. Note that raw solid nitroguanidine is added from storage 22 to the feed solution reservoir 24 to maintain the nitroguanidine concentration at $C_1$. The temperature in reservoir 24 is kept at constant $T_1$ by the following: (1) the capacity of the resevoir, (2) the flow of solution ($T_2$, $C_2$) from lines 30 and 38 into the reservoir 24, and (3) heating means.

The use of methylcellulose and partially hydrolyzed poly(vinyl alcohol) as a crystal modifier pair is critical to this invention. If no crystal modifier is used, or if methylcellulose alone or partially hydrolyzed poly(vinyl alcohol) alone is used as a crystal modifier, needleshaped or rodshaped nitroguanidine crystals are produced. However, when a mixture of methylcellulose and partially hydrolyzed poly(vinyl alcohol) is used as a crystal modifier, high bulk density spheroidal or egg-shaped nitroguanidine crystals (HBNQ) are produced. Preferably from about 0.5 to about 2.0 and more preferably from 0.6 to 1.0 weight percent of methylcellulose is used with from about 0.5 to about 2.0 and more preferably from 0.6 to 1.0 weight percent of partially hydrolyzed poly(vinyl alcohol) in the aqueous nitroguanidine solution.

Commercial methyl cellulose is used in the present process. The *Merck Index* (10th edition), page 866, monograph No. 5917, states that commercial methylcellulose (or methyl cellulose ether) has a methoxyl content of 29% (degree of substitution about 1.8) and that it is available under proprietary names such as Methocel, Cellothyl, Syncelose, Bagolax, Cethylose, Cethytin, Cologel Cellumeth, Hydrolose, Nicel, Tearisol, Tylose, etc.

Poly(vinyl alcohol) is prepared by the alcoholysis of poly(vinyl acetate). A 85 to 90% hydrolyzed (acetal content 15 to 10%) and preferably 87 to 89% hydrolyzed (acetal content 13 to 11%) poly(vinyl alcohol) is used in the present process. These partially hydrolyzed poly(vinyl alcohols) have good solubilities in water for both the high ($T_1$) and the low ($T_2$) temperature ranges of this process, with 87–89% hydrolyzed poly(vinyl alcohols) being optimal. The *Merck Index* (10th edition) page 1095, monograph No. 7458, provides information on and a list of proprietary names for poly(vinyl alcohol).

Other critical parameters of this process are the feed solution temperature $T_1$ and the crystallizer temperature $T_2$. These temperatures are selected to produce spheroidal or ovate high bulk density nitroguanidine crystals (HBNQ) at an efficient rate. The feed solution temperature $T_1$ is preferably in the range of 70° C.$\leqq T_1 \leqq$100° C. and more preferably in the range of 80° C.$\leqq T_1 \leqq$100° C. The concentration of the feed solution $C_1$ is the saturation concentration of nitroguanidine in water at $T_1$. The crystallizer solution temperature $T_2$ is defined in terms of the feed solution temperature. Preferably 20° C.$\leqq T_1 - T_2 \leqq$50° C. and more preferably 30° C.$\leqq T_1 - T_2 \leqq$40° C.

Particle size and distribution are determined primarily by the residence time of the crystals in the crystallizer 28. Other factors such as the nitroguanidine concentration or the agitation rate in the crystallizer do have influence but to a lessor extent. The residence time of crystals is controlled by the rate of the feed stream 26 into the crystallizer 28. When the crystals reach the desired size they fall to the bottom of the crystallizer 28 and are drawn off in the product stream 32.

The general nature of the invention having been set forth, the following examples are presented as specific illustrations thereof. It will be understood that the invention is not limited to these examples but is susceptible to various modifications that will be recognized by one of ordinary skill in the art.

In the following examples 1–14, processes were run under conditions which simulated a continuous process. A 3-liter beaker was used as the feed solution reservoir 24 and a 3-liter reactor with stirrer was used as the crystallizer 28 in the FIGURE. The concentrations of methycellulose and partially hydrolyzed poly(vinyl alcohol) were the same in both the beaker (feed solution resevoir) and the reactor (crystallizer) as they would be in a recycling continuous process. Specifically, the following procedure was used in examples 1 through 14:

1. Distilled water was heated by a hot plate in a 3-liter beaker to 68° C. (155° F.). Distilled water was also heated to 68° C. (155° F.) in a 3-liter reactor placed in a steam bath.

2. While being agitated, dry Methocel or partially hydrolyzed poly(vinyl alcohol) or a combination of both were added to the beaker and reactor.

3. The solutions in the 3-liter reactor and beaker were heated further to to 82° C. (180° F.), then cooled to below 32° C. (90° F.).

4. The solutions were then diluted with an equal volume of water and reheated to 82° C. (180° F.).

5. While being agitated, the desired concentrations of nitroguanidine (NQ) were added to the solutions.

6. The solution in the 3-liter beaker was heated to boiling. The solution in the reactor was heated to 96° C. (205° F.) and then cooled to the desired operating temperature.

7. While being agitated, the hot beaker of nitroguanidine solution was poured into the 3-liter reactor. The rate of addition was dictated by the rate of cooling, i.e., to maintain a constant temperature within the reactor.

8. Immediately after the addition was complete, the agitator was turned off and the crystals were allowed to settle.

9. The supernatant liquid was decanted off and the crystals were washed with distilled water in the 3-liter flask.

10. The crystals were collected on a fritted polyethylene Buchner funnel and then sent for analysis.

Equipment used:

3-liter beaker (as the feed solution resevoir)

Hot plate and magnetic stirrer

Thermometer 3-liter round-bottomed reactor (as the crystallizer)

Air operated agitator (round bottomed blade 8 cm×2 cm)

Steam bath

Vacuum source

Fritted polyethylene Buchner funnel

The reaction conditions and results of examples 1 through 14 are presented in Table 1.

TABLE 1

| | | CONTINUOUS RECRYSTALLIZATION RESULTS NITROGUANIDINE (NQ) | | | | | | |
|---|---|---|---|---|---|---|---|---|
| Experiment Number | Agitator Speed (rpm) | Temperature of Crystallizer | Temperature of feed Solution | NQ Concentration In Crystallizer % | NQ Concentration in Solution % | Additive(s)[1,2] Feed Solution and Crystallizer | Bulk Density g/cm$^3$ | Crystal Shape(s) |
| 1 | 500 | 50° C. | 100° C. | 0.0 | 5.0 | 0.6% Methocel | 0.56 | N |
| 2 | 450 | 37° C. | 100° C. | 0.0 | 5.0 | 0.6% Methocel | — | N |
| 3 | 500 | 31° C. | 100° C. | 0.0 | 5.0 | 0.6% Methocel | 0.59 | N |
| 4 | 400 | 70° C. | 100° C. | 2.2 | 5.0 | 0.6% Methocel | — | N |
| 5 | 200 | 70° C. | 100° C. | 2.2 | 5.0 | 0.6% VINOL 540<br>0.6% Methocel | 0.83 | N, G |
| 6 | 200 | 70° C. | 100° C. | 2.2 | 5.0 | 0.6% VINOL 540<br>0.6% Methocel | 0.91 | E |
| 7 | 300 | 52° C. | 100° C. | 0.8 | 4.0 | 0.6% VINOL 540<br>0.6% Methocel | 0.91 | E |
| 8 | 300 | 52° C. | 100° C. | 0.8 | 4.0 | 0.6% VINOL 540 | 0.72 | N, G |
| 9 | 250 | 52° C. | 100° C. | 0.8 | 4.0 | 0.6% % Methocel<br>0.6% VINOL 540 | — | E |
| 10 | 500 | 79° C. | 100° C. | 4.0 | 5.0 | 0.6% Methocel<br>0.6% VINOL 540 | — | N, G |
| 11 | 100 | 79° C. | 100° C. | 4.0 | 5.0 | 0.6% Methocel<br>0.6% VINOL 540 | 0.90 | N, G |
| 12 | 50 | 52° C. | 100° C. | 1.0 | 5.0 | 0.6% Methocel<br>0.6% VINOL 540 | 0.80 | N, G |
| 13 | 500 | 65° C. | 100° C. | 4.0 | 5.0 | 0.6% Methocel<br>0.6% VINOL 540 | 0.87 | E |
| 14 | 600 | 65° C. | 100° C. | 2.0 | 4.0 | 0.6% Methocel<br>0.6% VINOL 540 | 1.0 | E |

1. Crystal habit modifier concentrations are identical in the feed solution and in the crystalizer as they would be in a continously recycling process.
2. VINOL 540 is a partially hydrolyzed (87–89%) poly(vinyl alcohol) polymer [9002-89-5] (PVA) which is available from the Polymer Chemicals Division of Air Products and Chemicals, Inc. Box 538, Allentown, Pa 18105. A 4% aqueous solution of VINOL 540 has a viscosity of 22–26 CPS at 20° C. and a pH range of 4.0–6.0.
3. N = needleshaped, G = jagged granular, and E = egg-shaped (ovate)

Obviously, numerous modifications and variations of the present invention are possible in light of the above teachings. It is therefore to be understood that within the scope of the appended claims the invention may be practiced otherwise than as specifically described herein.

What is claimed is:

1. A continuous process for recrystallizing nitroguanidine comprising the following steps in order:

(1) forming a saturated aqueous nitroguanidine solution at a constant temperature $T_1$ which is in the range of from about 70° C. to about 100° C. wherein the solution also contains from 0.5 to 2.0 weight percent of methylcellulose and from 0.5 to 2.0 weight percent of a partially hydrolyzed poly(vinyl alcohol);

(2) feeding the solution formed in step (1) into a crystallizer containing a saturated aqueous solution of nitroguanidine which is maintained at a constant temperature of $T_2$ wherein 20° C.$\leqq T_1-T_2 \leqq$50° C. and wherein the methylcellulose and partially hydrolyzed poly(vinyl alcohol) concentrations are the same as in the feed solution;

(3) separating the product spheroidal or ovate nitroguanidine crystals from the supernatant aqueous nitroguanidine solution; and (4) recycling the separated supernatant aqueous nitroguanidine solution to be used again in step (1).

2. The process of claim wherein the solution in the crystalizer in step (2) is continuously agitated.

3. The process of claim 1 wherein 80° C.$\leqq T_1 \leqq$100° C.

4. The process of claim 3 wherein 30° C.$\leqq T_1-T_2 \leqq$40° C.

5. The process of claim 1 wherein 30° C.$\leqq T_1-T_2 \leqq$40° C.

6. The process of claim 1 wherein the concentration of methylcellulose in the aqueous nitroguanidine solutions is from 0.5 to 1.0 percent by weight.

7. The process of claim 6 wherein the concentration of partially hydrolyzed poly(vinyl alcohol) in the aqueous nitroguanidine solutions is from 0.5 to 1.0 percent by weight.

8. The process of claim 1 wherein the concentration of partially hydrolyzed poly(vinyl alcohol) in the aqueous nitroguanidine solutions is from 0.5 to 1.0 percent by weight.

* * * * *